United States Patent [19]

Desruelles et al.

[11] Patent Number: 4,918,989

[45] Date of Patent: Apr. 24, 1990

[54] ULTRASONIC METHOD OF MEASURING THE THICKNESS OF THE PLATING ON A METAL TUBE, THE CORRESPONDING APPARATUS AND ITS APPLICATION TO ZR PLATED ALLOY TUBES

[75] Inventors: Didier Desruelles, Albertville; André Bodin; Philippe Moinard, both of Montreuil Juigné, all of France

[73] Assignee: Compagnie Europeenne du Zirconium - CEZUS, Courbevoie, France

[21] Appl. No.: 321,071

[22] Filed: Mar. 9, 1989

[30] Foreign Application Priority Data

Mar. 30, 1988 [FR] France .................. 88 04726

[51] Int. Cl.$^5$ .................................. G01N 29/00
[52] U.S. Cl. ........................................ 73/627; 73/637
[58] Field of Search ................. 73/597, 614, 615, 616, 73/622, 627, 629, 637; 364/562, 563, 569

[56] References Cited

U.S. PATENT DOCUMENTS 4,512,194  4/1985  Beuter ............................ 73/602
4,625,556  12/1986  Sukahara et al. ............... 73/602
4,669,310  1/1987  Lester ............................. 73/629

FOREIGN PATENT DOCUMENTS 58-199139  11/1983  Japan .
60-14210   7/1985   Japan .
62-91806   4/1987   Japan .
62-204107  9/1987   Japan .

Primary Examiner—Hezron E. Williams
Assistant Examiner—Louis M. Arana
Attorney, Agent, or Firm—Dennison, Meserole, Pollack & Scheiner

[57] ABSTRACT

According to the method of the invention concerning tubes, of which the plating to be checked is at least 0.4 mm thick and in which the acoustic impedance differs by at least 1% relative from that of the core of the tube, a properly dampened transducer is selected which has a frequency of 4 to 10 MHz. The position of the transducer in respect to the tube is adjusted experimentally, and its parameters of distance and orientation are differently adjusted in order to increase the "signal-to-noise" ratio. For determining the thickness of the plating, at least one double echo from the interface between the plating and the tube core is used, or alternatively, a triple echo from this interface. Also, there is a corresponding ultrasonic measuring apparatus as well as an application of the method to the ultrasonic measuring of the thickness of the plating of Zr alloy tubes. The tubes are plated with non-alloyed Zr or with some other Zr alloy.

17 Claims, 4 Drawing Sheets

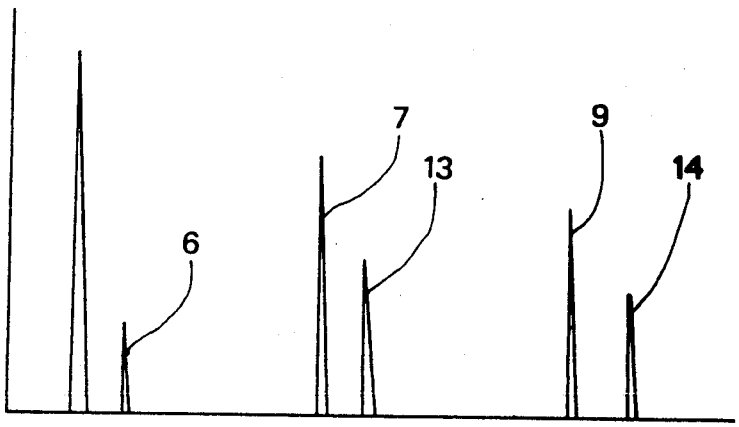
FIG.4
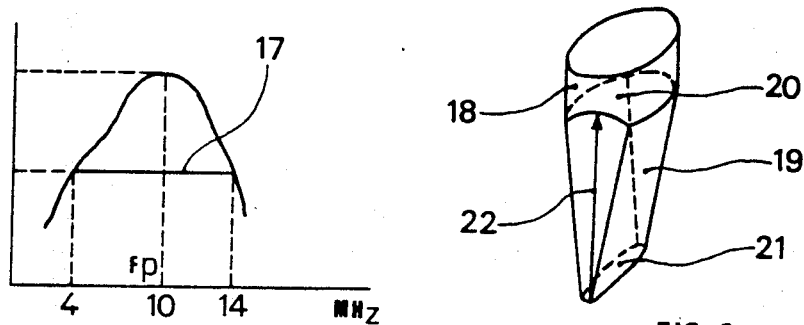
FIG.5
FIG.6
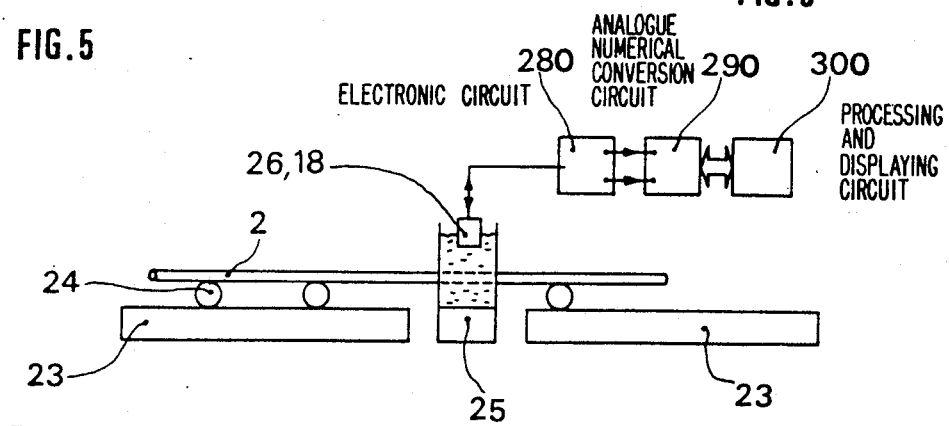
FIG.7

ULTRASONIC METHOD OF MEASURING THE THICKNESS OF THE PLATING ON A METAL TUBE, THE CORRESPONDING APPARATUS AND ITS APPLICATION TO ZR PLATED ALLOY TUBES

BACKGROUND OF THE INVENTION

The invention relates to the non-destructive checking of the thickness of the interior or exterior plating on metal tubes and more precisely to a method of and an apparatus for using ultrasonics to measure this thickness, and also to the application of this method to Zr plated alloy tubes.

The publication "Liner thickness measurement for zirconium lined Zircaloy cladding tube using dial frequency Eddy current method" by M. IWASAKI, N. SUZUKI, Y. NISHIMOTO, M. KOTANI and N. FUJII—Nuclear Engineering and Design 94 (1986)—pp. 447–452—describes a method of using Foucault currents for measuring the thickness of the internal non-alloyed Zr lining in Zircaloy tubes, this thickness being comprised between 40 um and 130 um approx. This method employs a probe which is displaced inside the tube while the tube rotates on itself. Other non-destructive measuring methods had been tried, particularly ultrasonic measuring which is "unusable because of the slight difference in acoustic impedance of Zircaloy and Zr".

Furthermore, the DERWENT abstract from the publication KOKAI JP-A-58 199 139 describes tubes comprising an external cladding of Zr alloy and an inner cladding of non-alloyed Zr, these two coatings being separated by an intermediate layer of graphite and methyl cellulose which makes it possible to use ultrasound to measure the thickness of the interior Zr cladding.

Wishing in particular to measure the thickness of the plating on Zr alloy tubes which are plated internally with non-alloyed Zr by metallurgical methods, these tubes typically having an outside diameter between 28 and 110 mm and an internal Zr plating thickness between 0.5 and 2 mm and constituting blanks for conversion to sheathing tubes, we noticed that since the use of Foucault currents for testing the interior of tubes required operations to achieve introduction into and then extraction from the interior of the tube to be checked, series inspection would be complicated and would not be very sensitive or would be difficult where the plating thicknesses exceeded 1 mm.

Notwithstanding the unfavourable indications in the first document and the supporting information provided by the second document, the we sought to perfect a non-destructive method of measuring the thickness of the interior lining from outside the tubes in question and wondered whether ultrasonic inspection would not nevertheless be possible.

STATEMENT OF THE INVENTION

The first object of the invention is a non-destructive method of measuring the thickness of the plating on a metal tube, the plating having a thickness of at least 0.4 mm and having an acoustic impedance different from that of the core of the tube to which it is metallurgically bonded, the difference being at least 1% relative, the check being carried out by ultrasound in immersion by means of a transducer or an emitter-receiver sensor, the method comprising at least the following stages:

(a) A properly damped transducer is selected, with a principal resonance frequency of between 4 and 20 MHz;

(b) The position of this transducer in relation to the tube is adjusted experimentally, its parameters of distance and orientation in respect of the tube being the subject of different adjustments in order to increase the "signal-to noise" ratio;

(c) To determine the thickness of the plating, at least one double echo from the plating/tube core interface is used, or a triple echo from this interface.

The method thus perfected is equally suitable for determining the thickness of an external plating as it is for an internal lining. The metallurgical connection of the plating originates typically from an application of this plating to the core of the tube under heat with deformation, for example co-extrusion or application by pressure under temperature, one or other application producing at least a very satisfactory adhesion of the plating and the core often with a slight diffusion in depth, for example 0.1 $\mu$m. The difficulties arise particularly from three points of view:

when the difference in acoustic impedance is small, for example around 2% relative, which corresponds to the difference between Zircaloy 2 and non-alloyed Zr, the ratio of the reflected wave to incident wave amplitudes which, in the case of an incident wave at right angles to the interface, is theoretically:

$$\frac{Z1 - Z2}{Z1 + Z2}$$

in which Z1 and Z2 are respectively the acoustic impedances of the two materials, is approx. 1% in accordance with this formula. It is then problematical whether an interface echo from noise or "grass" can be experienced;

the interface and the cylindrical inner and outer surfaces of the tube are substantially cylindrical, leading to an absence of reflections towards the transducer when the incident waves diverge from the perpendicular in relation to these surfaces;

furthermore, the geometrical axis of an ultrasonic transducer may be other than its acoustic axis and the acoustic field which it emits is not a field of revolution about this axis.

The method according to the invention is based on three types of measurement:

(a) measurements chosen by the transducer, satisfactory damping being required so that secondary resonances do not obscure detection and the oscillogram, the main frequency being chosen in such a way as to achieve suitable resolution;

(b) experimental adjustment of the transducer affecting its distance from and parameters of orientation in respect of the tube. In fact, the orientation of the geometrical axis of the transducer at right angles to the tube and fixing its distance from the tube or at the interface as a function of the known characteristics of the transducer probe to be inadequate if a good "signal-to-noise" ratio is to be achieved, that is to say a clear oscillogram in which background echoes and intermediate echoes emerge from the "grass". In our tests, we ascertained that it required both a well-chosen transducer and a completely "personalised" and usually iterative adjustment of the exact position of the transducer in order to obtain an oscillogram which brings out background echoes and interface echoes;

(c) finally, in the case of a tube with an interlining, it has been found that the first echo (6) from the interface (3) was not really usable for series measuring its emergence from the glass being irregular and insufficient. The same applies to the sound echo (16) from the interface (3), corresponding to a return path of the ultrasonic waves within the thickness, interrupted by a return path within the internal lining.

In this same case of an internally lined tube, it has been noticed that there was an interface echo of virtually twice the level (9), corresponding to two ultrasonic wave paths, each comprising a return path of these ultrasonic waves within the total thickness of the tube, either in this sequence or inverted. The resultant interface echo, here referred to as a "double interface echo", is therefore the sum of two echoes corresponding to two paths having the same travel time, the same core and lining thicknesses being traversed, but having a different reflection-transmission chronology. There are other "double interface echoes", each corresponding to two equivalent simultaneous paths of ultrasonic waves and having travel times greater than that of the first double interface echo. There are also "triple interface echoes" as from the third return path of the ultrasonic waves within the thickness of the tube and in some cases these may be of interest.

The most interesting of the "double interface echoes", particularly when the difference in acoustic impedance is small, for example between 1 and 15%, are those which correspond to two equivalent paths of the ultrasonic waves, each comprising only a single reflection on the interface. They then make it possible repetitively to monitor the thickness of the internal lining or outer cladding on a tube.

When the difference in acoustic impedances in the plating and the core of the tube is small, it is important that the ultrasonic transducer employed gives a very clear energy pulse with a width at half the height of its energy spectrum according to the frequency which is at least equal to half its principal resonance frequency. This principal resonance frequency is preferably between 8 and 16 MHz, and the width of the said spectrum is in any case preferably between 0.7 times and twice the principal resonance frequency.

The smaller the difference in acoustic impedances and the smaller the diameter of the interface, the more important it is to have a strong concentration of ultrasonic energy and proper location of this energy at the level of the interface. It is then if not indispensable then certainly at least often preferable to have a focusing transducer and better still a "cylindrical focusing" transducer, i.e. a transducer with a cylindrical free surface, of which the acoustic beam tapers out into a narrow and elongated focal zone, both in water and in the item being checked. Adjustment of the position of the transducer therefore is aimed at placing this elongated focal zone on a longitudinal generatrix of the interface to be detected, making it possible to minimize ultrasonic energy losses due to oblique reflections on this interface and also to improve the coverage or proximity of adjacent measurements of the lining thickness.

As has been touched upon already, it is necessary furthermore to place the ultrasonic wave which is propagated within the immersion liquid, typically water, then in the piece, in such a way that the energy reflected on the interface and on the inner and outer surfaces of the tube is at a maximum, requiring the position to be adjusted by successive tests, parameter by parameter. Usually, with a suitable carrier, that is to say one which makes it possible to maintain a fixed position of the transducer in relation to the tube or series of tubes monitored, the transducer is orientated virtually at a right angle to the axis of the tube which its distance from the tube is adjusted and the transducer is displaced transversely until the background echo or echo from the inner surface of the tube is clearly distinguishable. After having possibly made a final adjustment of one or more of these first three parameters in order to obtain or improve the detection of this background echo, two other means of adjusting the transducer are acted upon which respectively control the rotation of the transducer about its own axis, that is to say its rotation on itself, and the inclination of this transducer according to the axial plane of the tube passing through the axis of the transducer or according to a plane which is parallel with it. Then there is a fine adjustment in which the two parameters are linked and correspond diagrammatically to the best orientation of the acoustic axis of the transducer and of its most favourable energy zone, for example its focal zone, in relation to the tube and its interface. It may be necessary to resume this 'fine tuning' by acting on at least a part of the four adjustments (distance, transverse position, position about its own axis and angle of inclination) until, at least as far as the second background echo, both background echoes and one or more interface echoes are obtained, comprising at least one "double interface echo".

In cases of measuring the thickness of the internal lining of a tube, it is then possible to determine this plating thickness as corresponding to:

either the interval separating the first double interface echo or double interface echo from the second passage of the ultrasonic waves, from the second background echo which is in this case the interval between two successive and quite separate echoes, which is particularly convenient to cope with electronically;

or alternatively, to improve the accuracy, to the half-interval separating the double interface echo from the second path of the second double interface echo which is the first double interface echo of the third path.

Other solutions are possible, for example that of using the offset between second background echo and second double interface echo, but beyond that it is possible to be hampered by the echoes of multiple parasite reflections.

Where measuring the thickness of the outer cladding is concerned, there are also many solutions based on taking into account at least one double interface echo, the first of which determines this cladding thickness on a basis of the interval between the first background echo and the first double interface echo.

For the continuous checking of a tube or series of tubes, it is desirable to maintain the position of the ultrasonic transducer rigorously constant in relation to the portions of tubes to be checked and also to maintain immersion in the inspection vessel, despite the succession of tubes, spaced apart or at contiguous ends. To obtain these results, the tubes are preferably drawn through a local immersion tank provided with inlet and outlet lock chambers, proximity detectors controlling the opening and closing of the double openings of the lock chambers in order to maintain immersion of the transducer and the portions of tube to be checked, making it possible to avoid any waiting time between two tubes which might be linked to the ultrasonic monitor; furthermore, the transducer carrier is applied to the tube during the course of ultrasonic inspection in a reproducible fashion thanks to suitable and typically rolling or sliding contact means carried by the support, the lowering of the support into a position where it is bearing on each tube, and also its removal therefrom, once the tube is checked and cleared, being produced by detectors which identify the fact that the ends of the tubes are passing by. All these arrangements make it possible to maintain quality of ultrasonic inspection of the thickness of plating for a series of tubes in one and the same batch and in different batches and of any dimensions, the individual lengths of the tubes varying considerably in every case, and with the minimising of the ultrasonic inspection time, these arrangements produce a considerable reduction in operator intervention.

A second object of the invention is an ultrasonic inspection apparatus which must of necessity be used in order to carry out the method according to the invention, the inspection being carried out with an ultrasonic transducer used on the emission-reflection basis, the principal reference frequency being preferably between 4 and 20 MHz and even more preferably still between 8 and 16 MHz, this apparatus comprising at least the following means:

independent adjustment means for the parameters of distance and orientation of the position of the transducer in relation to the tubes to be inspected;

means of tracking this position in the case of successive tubes of the same type;

electronic means adapted to detect at least one double (plating/tube core) interface echo.

In accordance with an advantageous embodiment, these control means form part of a support member comprising: a transducer slide support comprising at least one means of regulating the transverse position of the transducer and a means of controlling its rotation about its own axis, this slide support being itself adjustably mounted for rotation about a transverse axis on a member which is regulated in its position in respect of uprights which are subject to the action of a jack connected to a fixed point. And the follow-up or tracking means comprise means of applying the aforesaid assembly, the members carried by the uprights carrying applying means which slide or roll on the tube to be checked, for example balls or rotating wheels.

The tube tracking or follow-on means preferably comprise furthermore a facility for the support member to rotate about a fixed axis parallel with the longitudinal axis of the tubes, through an upper member in which the uprights slide, usually in a midway position between the regulating member which is rigid with the slide support, for the transducer and the supporting jack. The combination of having the jack support the support member and of this facility for rotation makes it possible to follow the sag in the tubes, typically less than 5 mm/m, whatever their orientation may be.

In the event of a local immersion tank being used, through which the tubes pass, two additional means which make it possible for continuous inspection of a series of tubes in automatic succession, avoiding any intervention by an operator or waiting time caused by the need to immerse the tube to be inspected and also the transducer, will be described in the example.

A third object of the invention is the application of the inspection method described to the ultrasonic inspection and monitoring of interior lining or external cladding of tube(s) of zirconium alloy plated with non-alloyed Zr or some other alloy of Zr, provided that the differences in acoustic impedance of the two metals or alloys in question is at least 0.8% relative, this difference generally being between 1 and 4% relative. Thus it is possible to measure the thickness of the interior lining of tubes of Zircaloy 2 or 4 plated on the inside with non-alloyed Zr.

In the case of "Triplex" tubes which have for instance an interior lining of non-alloyed Zr, a Zircaloy core and an outer cladding of Zr-Fe 0.12 to 0.24%—V 0.13 to 0.3%—Sn and Nb each of less than 0.15%, this outer cladding having a remarkable resistance both to uniform corrosion and to nodular corrosion, it is possible successively to inspect the thicknesses of these two platings, with the transducer being adjusted in position to suit each case.

This indication is applied to tubes having an internal and an external plating of other metals or alloys.

BRIEF DESCRIPTION OF THE DRAWINGS

FIG. 4 shows the corresponding echoes on the oscillogram.

FIG. 5 shows the spectrum of frequency of the ultrasonic transducer used.

FIG. 6 represents the acoustic field of the same transducer, in an isometric projection.

FIG. 7 is a diagram showing the general arrangement of the test bench used.

DESCRIPTION OF THE PREFERRED EMBODIMENT

1. Ultrasonic testing principle employed

Figure 1:
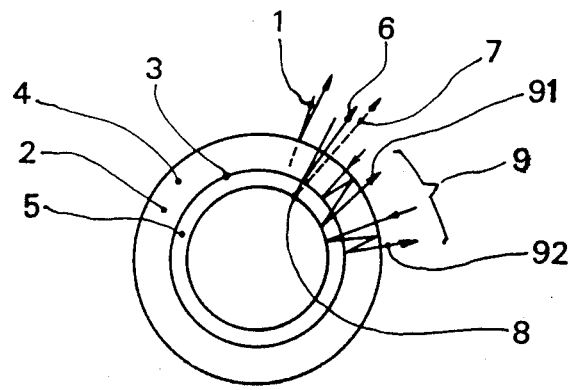
FIG. 1 shows the paths of ultrasonic waves in a tube with an interlining, the drawing representing a cross-section through the tube.
Figure 2:
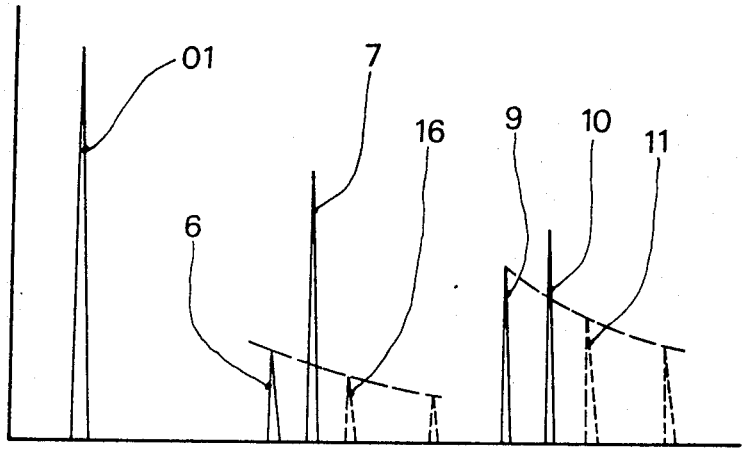
FIG. 2 represents the corresponding echoes on the oscillogram.

The ultrasonic wave 1 at right angles to the surface of the tube 2 (FIG. 1) is reflected partially on this surface, giving an initial echo 01, is propagated in the tube in a direction at right angles to the interface 3 between the core 4 and the plating 5 and is reflected partially on this interface 3 and is transmitted partially into the plating or cladding 5. Thus, from this first reflection on the interface 3, there is a direct return 6 towards the transducer yielding the first echo 6 from the interface 3 on the oscillogram (diagram in FIG. 2), situated in front of the first background echo 7 or direct reflection echo from the interior surface 8 of the tube 2. This interface echo 6 is situated at a distance from the background echo 7 corresponding to the thickness of the plating 5, but if the acoustic impedance of the core is close to that of the plating, it cannot be used for continuous or series monitoring because there is a relatively small amplitude and the zone preceding the first background echo 7 is often disturbed by resonance and parasite echoes.

It has been found that among the subsequent echoes emanating from the interface 3, there was an echo 9 situated in front of the second background echo 10, which was particularly interesting: by virtue of its height which was practically twice that of the first interface echo 6, and because in addition it is in a less disturbed zone of detection. Interpretation is as follows: a part of the acoustic energy reflected on the interface is reflected again in the complete thickness of the tube, yielding an echo 91, the situation of which takes into account two paths within the total thickness of the tube less one return path in the thickness of the plating.

A different journey but equivalent in travelling time in the tube 2 is obtained by reflection on the interior surface 8 of the tube 2 and return 92 towards the transducer interrupted by two reflections respectively on the interior of the outer surface of the tube 2 and on the interface 3, that is to say by a return path within the thickness of the core 4. These two paths of equivalent duration are produced in such a way that the echo 9 at a thickness of plating 5 in front of the second background echo 10 is the sum of the two returns of energy or simultaneous echoes 91 and 92. With the subsequent reflections and transmissions, further "double interface echoes" are obtained which can be used for monitoring purposes, particularly the double echo 11 in FIG. 2 corresponding to two equivalent paths of the ultrasonic waves comprising each two return paths within the total thickness of the tube 2 and one return path, within the thickness of the plating 5, and, situated at "a thickness of the plating" after the second background echo 10, an echo 11 of which the important interest is the possibility of direct measurement of twice the thickness of the plating 5 between the double interface echoes 9 and 11, improving the accuracy with which this thickness is estimated.

Figure 3:
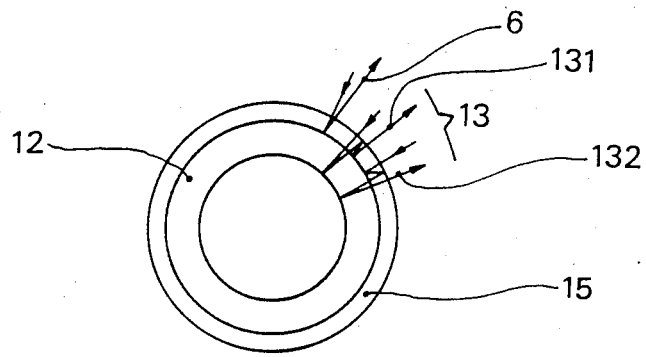
FIG. 3 represents the paths of ultrasonic waves in a tube with an outer cladding.

Similar phenomena are produced during ultrasonic testing of an externally clad tube 12 (FIGS. 3 and 4) and thus, over and above the first interface echo 6 and the first background echo 7, a first double interface echo 13 is obtained which is the sum of two equivalent paths in time 131 and 132, each comprising a return path within the thickness of the tube 10 and one round trip in its outer cladding 15. The subsequent triple echo 14 results from three simultaneous paths to one single reflection on the interface, each comprising two round trips in the thickness of the tube 12 and one round trip in the core or internal coating of the tube, this echo 14 being situated at one "plating thickness" after the second background echo 9.

2. Plated tubes examined

The tubes checked were a batch of Zircaloy 2 tubes plated on the inside with non-alloyed Zr. The plating was carried out by co-extrusion at 650° C., the extruded composite blanks obtained being reduced by cold rolling and then annealed after rolling. The dimensions were: outside diameter 63.5 mm × total thickness 10.9 mm with a mean plating thickness of 1.5 mm; mean length 5 m (individual lengths ranging from 1.5 to 6 m).

3. Monitoring equipment (3.1) Ultrasonic transducer selected

This was a transducer 18 having a principle frequency $Fp=10$ MHz, of the cylindrical focusing type, the transducer diameter being $\frac{1}{2}''=12.6$ mm. Properly damped, this transducer had a width 17 at half the height of its frequency spectrum, or energy diagram or amplitude of signal transmitted as a function of the vibration frequency (FIG. 5) of 10 MHz, that is to say of the same value as its principal frequency Fp. FIG. 6 diagrammatically shows the structure of the cylindrical focusing transducer 18 and the form of its acoustic pulse 19, the free surface 20 of this block of transducer 18 being concave cylindrical and the pulse 19 thinning out and becoming concentrated in a focal zone 21 which is narrow and elongated, parallel with the rectilinear generatrices of the face 20. The focal distance 22 here is 40.6 mm in water, the width and length of the total zone being approx. $0.5\times3$ mm.

(3.2) Inspection apparatus

It comprises (FIG. 7) a bench or frame 23 for the supply and delivery of tubes 2 carried along an inclined plane then caused to rotate on a line of pairs of rollers 24 in order to regulate the pitch and therefore the rate of feed. The tubes 2 of the batch being tested are in this case driven at a speed of rotation about themselves of 250 revolutions/min with a rate of feed of 1 m/min, each point on their surface describing a helix or spiral of which the pitch is 4 mm. Defects in the straightness of the tubes are small, the amount of sag all being less than 1.5 mm per meter. The tubes are thus pushed through a local immersion tank 25 which is filled with water through its base. This tank 25 comprises an inlet lock chamber for the tubes and also an outlet lock chamber, not shown, each lock chamber comprising an outer lid or cover masking the outside aperture by pivoting over or away from this aperture under the action of inductive detectors which sense the proximity of the tubes, and a wall or sealing tight interior sliding diaphragm which closes or opens the inside aperture following or preceding the said outer aperture, likewise under the effect of position detectors.

Figure 8:
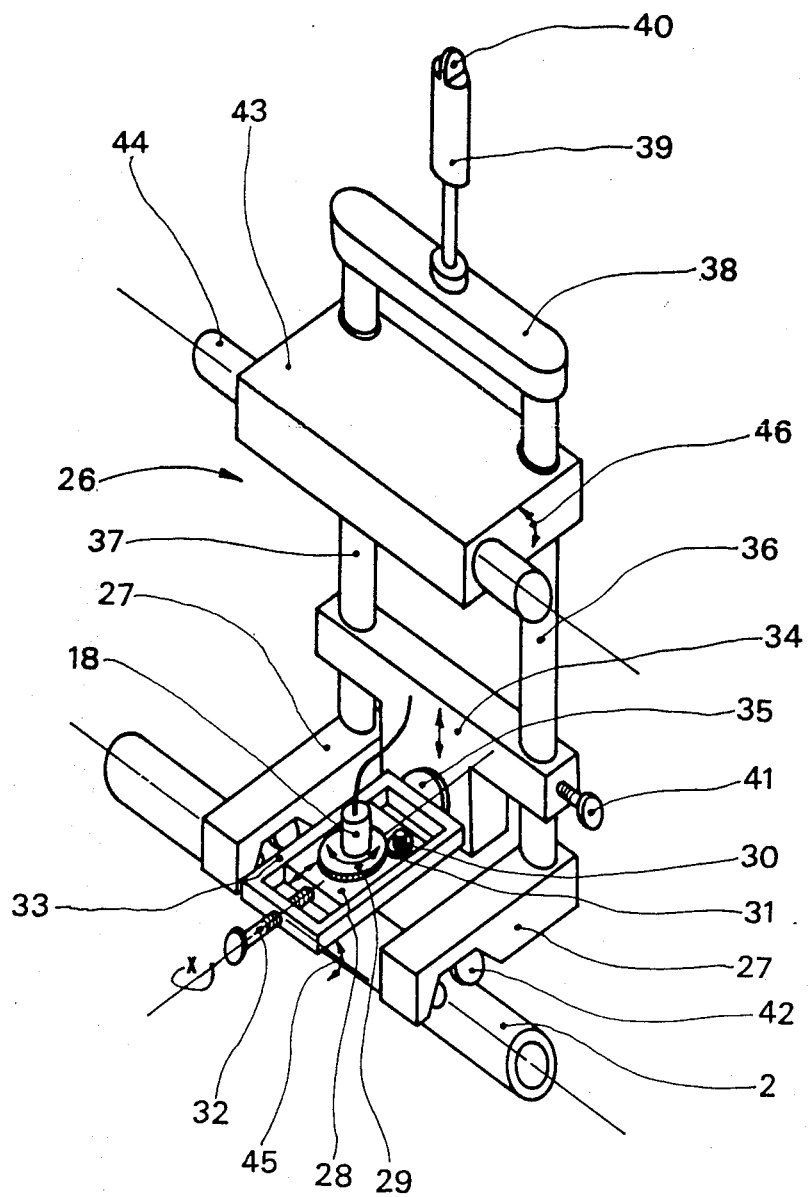
FIG. 8 shows the transducer support member in an isometric projection.

When a tube 2 has entered the immersion tank 25 and arrives close to the central monitoring position, the support member 26 of the transducer 18 lowers automatically under the effect of immersed proximity detectors, its support means 27 (FIG. 8) coming in contact with the tube 2 and the transducer 18 finds again exactly its former position or the regulated position in relation to the tube 2. The support member 26 lifts off again as soon as inspection is completed.

The emitter-receiver transducer 18 is connected to electronic elements 280 comprising an emitter and a receiver with a broad frequency band, with a high-gain amplifier (at least 80 dB), a peak detection system and a device for correcting the gain according to the distance. Then there are elements for automatically processing the results, comprising rapid analogue-numerical conversion circuit 290 and a processing and displaying circuit 300 to view the results.

(3.3) Transducer regulating and follow-up or tracking means

The support member 26 (FIG. 8) comprises a support 28 sliding inside a frame 33 on which the transducer 18 is mounted by means of a disc 29 having a notched edge and capable of being rotationally rigid with a second notched member 31 by means of a screw 30, the rotation of the disc 29 making it possible to regulate the position of this transducer in rotation about itself. A screw 32 passing through the front of the frame 33 serves to regulate the transverse position of the support 28 and therefore of the transducer 18. The back of the frame 33 is fixed on a T-shaped vertical member 34 by means of a disc 35 resting on the face of the T and adapted to rotate about an axis X at right-angles to the axis of the transducer 18 and to the face of the T, the axis X being parallel with the direction of transverse slide of the support 28. The means of rotationally locking the disc 35 and the level for rotationally entraining the slide support 28 and 32 about the axis X are not shown.

The T-shaped member 34 slides along two substantially vertical rods or columns 36 and 37, the top ends of which are housed in a cross member 38 to which is fixed the stem of a hydraulic jack 39 providing a suspension and thrust means, the jack 39 being attached at a fixed point 40. The T-shaped member 34 may be locked on the columns 36 and 37 by two screws such as 41, the height of the transducer 18 above the tube 2 to be checked thus being regulated.

The columns 36 and 37 carry at their bottom ends two transverse bearing members 27, each of which has on its underside a V-shaped notch provided with two freely rotating teflon rollers 42 adapted to straddle the tube 2. These bearing members 27 and therefore the rollers 42 can be orientated in the same way as the rollers 24 outside the tank 25, facilitating the movement of the tubes 2 and avoiding or restricting friction of and wear and tear on the rollers 42.

In addition to the bearing members 27 which are subjected to pressure from the jack 39, the follow-up or tracking means comprise a top plate 43 which is free to rotate about a longitudinal axis 44, the uprights or columns 36 and 37 slidingly traversing the rear of this top plate 43.

The slide support 28 and frame 33 of the transducer 18 are therefore able to turn easily like the plate 43, as indicated by the double-headed arrows 45 and 46, improving the contiguous positioning of the slightly deflected tubes.

4. Measuring conditions and results

The position of the transducer 18 has been regulated according to the experimental method already described. The transducer was energised at a frequency of 1 kHz so that there were 240 measurements taken per rotation of the tube. The position of the double interface echo 9 and of the second background echo 10 (FIG. 2 and FIG. 9) were recorded and the time 47 between these two echoes 9 and 10 was converted into thickness.

Figure 9:
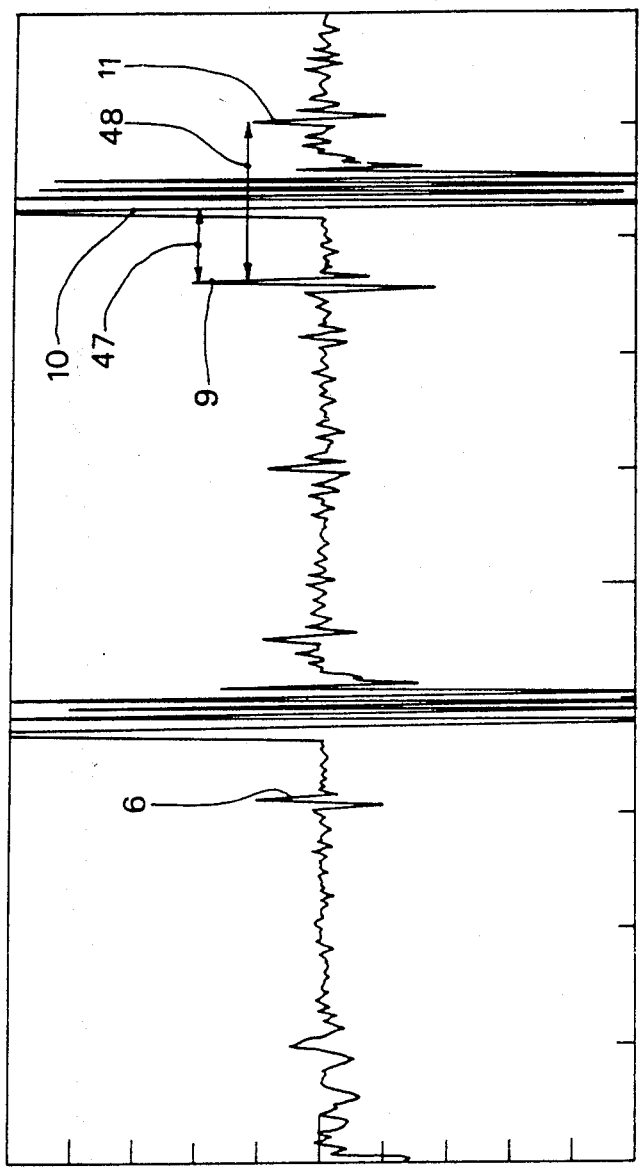
FIG. 9 is an oscillogram taken from the testing of a series of tubes.

In FIG. 9, which shows a real oscillogram of this inspection, there is recorded with the first interface echo 6, which it is difficult to use on a series basis, the double interface echoes 9 and 11, as well as the time 47 separating the echoes 9 and 10, representing the thickness of the inner plating and twice the time 48 separating the first double echo 9 from the second double interface echo 11.

The values for plating thickness corresponding to each turn of the tube were treated statistically and recorded, and the positions of the portions of the tube of which the plating thickness was outside the tolerance were marked for subsequent rejection. The accuracy of the plating thickness measurement thus carried out was of ±3 μm.

A few divergent measurements, in other words 5 to 15 measurements per turn of the tube representing 240 measurements, were not taken into account. These diverging measurements above all represent anomalies in reflection of the interface.

ADVANTAGES OF THE INVENTION

It permits of accurate ultrasonic measurement of the thickness of internal and external cladding on a plated tube, despite a very slight difference in acoustic impedance;

this inspection is carried out from the outside and continuously, which is advantageous for series production and automation;

the apparatus permits of reproducible settings with no need for readjustment between tubes of one and the same series or batch of the same composition and same geometry;

this ultrasonic inspection permits of precise cropping of those tube portions in which the plating thickness is outside the tolerances, for example corresponding to the commencement of extrusion, this advantage providing substantial saving on material and quality safeguards.

We claim:

1. A method for non-destructive measuring a thickness of a plating metallurgically bonded on metal tubes, said each tube having a core with an acoustic impedance, and said plating with a thickness of at least 0.4 mm and an acoustic impedance interfacing said core impedance, wherein said plating impedance differs from said core impedance by at least 1.0%, said method using an emitter-receiver transducer in immersion positioned outside said tube for producing ultrasonic waves to generate at least a single echo through said tube, wherein said method comprises the following steps:
    selecting a properly dampened transducer with a principal resonance frequency between four and 20 MHz as said emitter-receiver transducer;
    positioning said transducer in relation to said tube at a distance as well as orientation to generate a distance parameter and orientation parameter, wherein said parameters with the produced ultrasound waves form a signal-to-noise ratio which is increased by adjusting said parameters; and
    determining the thickness of said plating from at least one double echo or a triple echo generated at said interfacing of said plating and said core, wherein said double and triple echoes correspond respectively to two or three return paths of the ultrasonic waves having the same travel time but a different reflexion-transmission chronology.

2. A method according to claim 1, wherein said step of selecting includes selecting said transducer with an energy spectrum according to a frequency with a width of half way up the spectrum, wherein the spectrum is at least equal to 0.5 times the principal resonance frequency.

3. A method according to claim 2, wherein said step of selecting includes selecting said transducer with a principal resonance frequency between 8 and 16 MHz and an energy spectrum according to the frequency with the width at half the height of the spectrum, wherein the spectrum is between 0.7 and 2.0 times the principal resonance frequency.

4. A method according to claim 3, wherein said step of selecting includes:
    selecting a cylindrical focusing transducer as said transducer; and
    disposing said transducer in relation to said tube so a focal point of said transducer is orientated along a longitudinal direction of said tube.

5. A method according to claim 1, wherein said step of positioning said transducer in relation to said tube includes the following steps;
    orientating said transducer with a support means so said transducer is very nearly at right-angles to a longitudinal axis of said tube;
    adjusting the distance parameter between said transducer and said tube by moving said transducer transversely in relation to said tube for clearly determining a background echo;

rotating said transducer by a regulating means about a longitudinal axis and on an inclination of said transducer according to the axis of said tube; and resuming said method of measuring the thickness of said plating by performing at least one of the steps of adjusting for increasing said signal-to-noise ratio, wherein at least two first paths of said ultrasonic waves generate first and second background echoes in said tub for determining one or a plurality of interface echoes from said interface of said plating and core.

6. A method according to claim 5, wherein said step of determining includes:

deriving said double echo at said interface from two equivalent paths of said ultrasonic waves, wherein each wave generates only a single reflection on said interface.

7. A method according to claim 6, comprising the step of:

determining an internal thickness of said plating by calculating an interval separating said double echo formed by the second path of said ultrasonic waves and said second background echo.

8. A method according to claim 6, comprising the step of:

determining an internal thickness of said plating by calculating half an interval separating said double interface echo formed by the second path of the first double interface echo and the third path.

9. A method according to claim 6, comprising the step of:

determining an external thickness of said plating by calculating an interval separating the first background echo from the double interface echo formed by the second path of said ultrasonic waves.

10. A method according to claim 9, wherein the ultrasonic inspection of the thickness of the internal plating or external plating of each said tube includes zincronium alloy plated with non-alloyed zirconium or other zincronium alloy with the outside diameter of said tube falling in the range of 28 mm to 110 mm while the thickness of said plating is between 0.4 mm and 0.5 mm the total thickness of said tube.

11. A method according to claim 10, wherein said internal plating comprises Zr alloy 2 or 4 on the inside with non-alloyed Zr.

12. A method according to claim 1, comprising the steps of:

conveying said tubes through a local immersion tank;

providing said tank with an inlet lock chamber and an outlet lock chamber;

controlling the opening and closing of said lock chambers with proximity detectors by maintaining immersion of said transducer and said tubes in which a support means applies said transducer in a reproducible fashion to said tube for inspection by an ultrasonic means;

bearing said support means on said tube through a suitable contact means by lowering said support means into a position so said contact means rests on each said tube controlled; and raising said contact means after delivery of said tube by registering the passage of each end of said tube by said proximity detectors.

13. An apparatus for ultrasonic inspection of immersed plated metal tubes, said plating of each tube having a thickness of at least 0.4 mm and an acoustic impedance, each said tube having a core which interfaces said plating and has an acoustic impedance which differs from said plating impedance by at least 1.0%, said apparatus including an ultrasonic transducer operating by an emission-reflection principle, and comprising:

independent regulating means for adjusting position parameters controlling distance and orientation of said transducer in relation to inspection of said tubes;

follow-up means for tracking the position parameters for each said tube and any successive tube;and electronic means for detecting at least one double echo at the interface between said plating and core of said tube.

14. An apparatus according to claim 13, comprising:

slide support means for mounting said ultrasonic transducer including means for regulating said transducer in a transverse direction; means for rotatably controlling said transducer about an axis of rotation; and wherein said slide support means is adjustably fixed for rotation about a member and each adjustable position is subjected to a jack connected to a fixed point;

upright carrying members for supporting said transducer near said tube during monitoring; and means for sliding said tubes into position of inspection by said transducer.

15. An apparatus according to claim 14, wherein said upright carrying members slide through a tip member which rotates about an axis parallel to a longitudinal axis of said tube so when said tubes sag, said follow-up means maintain tracking with said transducer.

16. An apparatus according to claim 14, comprising:

a tank for immersion of said transducer and a portion of said tube being inspected;

proximity detectors for detecting the passage of each end of said tube; and control means for controlling the movement of said support means so said transducer inspects each tube and then is removed after said tube passes through the inspection.

17. An apparatus according to claim 16, wherein said tank comprises:

an inlet lock chamber and a outlet lock chamber, each said chamber including an exterior moveable cover and an interior moveable double wall with the movements of said walls controlled by said proximity detectors which detect passage of the ends of said tubes so immersion of successive tubes is maintained.

* * * * *

UNITED STATES PATENT AND TRADEMARK OFFICE
CERTIFICATE OF CORRECTION

PATENT NO. : 4,918,989
DATED      : April 24, 1990
INVENTOR(S) : Didier Desruelles, et al It is certified that error appears in the above-identified patent and that said Letters Patent is hereby corrected as shown below:

Column 11, line 9, "tub" should read --tube--

Column 11, lines 40-41, "zincronium" should read --zirconium--

Column 11, line 42, "zincronium" should read --zirconium--

Signed and Sealed this

Thirteenth Day of August, 1991

Attest:

HARRY F. MANBECK, JR.

*Attesting Officer*   *Commissioner of Patents and Trademarks*